(12) United States Patent
Schulte et al.

(10) Patent No.: US 8,494,619 B2
(45) Date of Patent: Jul. 23, 2013

(54) SYSTEMS AND METHODS FOR THE GENERATION AND DISPLAY OF FUSION STATISTICS

(75) Inventors: Theodore J. Schulte, Austin, TX (US); Yanting Dong, Shoreview, MN (US); Shibaji Shome, Minneapolis, MN (US); Abhilash Patangay, Inver Grove Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 448 days.

(21) Appl. No.: 12/781,411

(22) Filed: May 17, 2010

(65) Prior Publication Data

US 2010/0305646 A1     Dec. 2, 2010

Related U.S. Application Data

(60) Provisional application No. 61/217,115, filed on May 27, 2009.

(51) Int. Cl.
*A61B 5/0452*    (2006.01)

(52) U.S. Cl.
USPC .......................................... 600/509

(58) Field of Classification Search
USPC .......................................... 600/509
See application file for complete search history.

(56) References Cited

U.S. PATENT DOCUMENTS

| | | | |
|---|---|---|---|
| 6,038,474 A | 3/2000 | Zhu et al. | |
| 6,456,881 B1 | 9/2002 | Bornzin | |
| 6,904,321 B1 | 6/2005 | Bornzin et al. | |
| 6,941,167 B2 | 9/2005 | Stahmann et al. | |
| 7,319,900 B2 | 1/2008 | Kim et al. | |
| 7,477,932 B2 | 1/2009 | Lee et al. | |
| 7,499,751 B2 | 3/2009 | Meyer et al. | |
| 7,555,340 B2 | 6/2009 | Dong et al. | |
| 7,574,260 B2 | 8/2009 | Stalsberg et al. | |
| 2002/0077859 A1 | 6/2002 | Stahmann et al. | |
| 2005/0131476 A1* | 6/2005 | Kim et al. | ........................ 607/27 |
| 2005/0131477 A1 | 6/2005 | Meyer | |

(Continued)

FOREIGN PATENT DOCUMENTS

JP          2008515485 A       5/2008

OTHER PUBLICATIONS

"International Application Serial No. PCT/US2010/035116, International Search Report mailed Aug. 6, 2010", 4 pgs.

(Continued)

*Primary Examiner* — Eric D. Bertram
(74) *Attorney, Agent, or Firm* — Schwegman Lundberg & Woessner, P.A.

(57) ABSTRACT

In an example, a cardiac rhythm management system includes an implantable physiological data monitor, a processor, a memory, and a display. The implantable physiological data monitor can be configured to monitor a plurality of cardiac responses. The processor can be configured to classify the cardiac response into one of at least three classes including pace-dominant, fusion, and pseudo-fusion. The processor can also be configured to calculate statistical information regarding the classified cardiac responses. In this example, the pace-dominant, fusion, and pseudo-fusion classes correspond to a cardiac response resulting from a corresponding electrostimulation. The memory is configured to store the classified cardiac responses and calculated statistical information for future use by the processor or for display. The display is configured to display the statistical information stored in the memory for diagnostic and device programming purposes.

22 Claims, 12 Drawing Sheets

U.S. PATENT DOCUMENTS

| | | | |
|---|---|---|---|
| 2005/0187588 | A1 | 8/2005 | Stahmann et al. |
| 2006/0224198 | A1 | 10/2006 | Dong et al. |
| 2006/0247707 | A1 | 11/2006 | Meyer et al. |
| 2007/0129766 | A1 | 6/2007 | Kim et al. |
| 2008/0119903 | A1* | 5/2008 | Arcot-Krishnamurthy et al. ............... 607/17 |

OTHER PUBLICATIONS

"International Application Serial No. PCT/US2010/035116, Written Opinion mailed Aug. 6, 2010", 8 pgs.

"Insignia Physician Manual", *Therapy; Basic Brady Parameters—Amplitude*, 6-12-6-17.

Bertini, Matteo, et al., "Automatic Verification of Ventricular Stimulation: Fusion Management Algorithm", *PACE*, vol. 31, (Jan. 2008), 64-69.

Boriani, Giuseppe, et al., "Evaluation of Fusion Beat Detection with a New Ventricular Automatic Capture Algorithm in ICDs", *PACE*, vol. 28, Supplement 1, (Jan. 2005), S263-S266.

Kamath, Ganesh S., et al., "The Utility of 12-Lead Holter Monitoring in Patents with Permanent Atrial Fibrillation for the Indentification of Nonresponders After Cardiac Resynchronization Therapy", *Journal of the American College of Cardiology*, vol. 53, No. 12, (Mar. 24, 2009), 1050-1055.

"Japanese Application Serial No. 2012-513100, Office Action mailed May 14, 2013", 2 pgs.

* cited by examiner

SYSTEMS AND METHODS FOR THE GENERATION AND DISPLAY OF FUSION STATISTICS

CROSS-REFERENCE TO RELATED APPLICATIONS

This application claims the benefit of U.S. Provisional Application No. 61/217,115, filed on May 27, 2009, under 35 U.S.C. §119(e), which is hereby incorporated by reference in its entirety.

This patent application is related to U.S. patent application Ser. No. 11/116,544, now published as U.S. 2006/0247707, and entitled "Cardiac signal template generation using waveform clustering," filed on Apr. 28, 2005. U.S. patent application Ser. No. 11/116,544 is hereby incorporated by reference into this application.

This patent application is also related to U.S. patent application Ser. No. 11/097,460, published as U.S. 2006/0224198, entitled "Electrogram Morphology-Based CRT Optimization," filed on Apr. 1, 2005. U.S. patent application Ser. No. 11/097,460 is hereby incorporated by reference into this application.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2009, Boston Scientific Corp. All Rights Reserved.

BACKGROUND

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, can be used as an effective treatment for patients with serious arrhythmias. These systems can comprise circuitry to sense electrical signals from the heart and a pulse generator for delivering electrical stimulation pulses to the heart. Leads extending into the patient's heart can be connected to electrodes that contact the myocardium for sensing the heads electrical signals and for delivering stimulation pulses to the heart in accordance with various therapies for treating the arrhythmias.

Cardiac rhythm management systems can operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses can be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal preceding the contraction can be denoted the captured response (CR). The captured response typically includes an electrical signal, denoted the evoked response signal, associated with the heart contraction, along with a superimposed signal associated with residual post pace polarization at the electrode-tissue interface. The magnitude of the residual post pace polarization signal, or pacing artifact, can be affected by a variety of factors including lead polarization, after-potential from the pace pulse, lead impedance, patient impedance, pace pulse width, and pace pulse amplitude, for example.

A pace pulse should exceed a minimum energy value, or capture threshold, to produce a contraction. It can be desirable for a pace pulse to have sufficient energy to stimulate capture of the heart without expending energy significantly in excess of the capture threshold. Thus, accurate determination of the capture threshold can be helpful for efficient pace energy management. If the pace pulse energy is too low, the pace pulses may not reliably produce a contractile response in the heart and can result in ineffective pacing. If the pace pulse energy is too high, the patient can experience discomfort and the battery life of the device will be shorter.

Detecting if a pacing pulse "captures" the heart and produces a contraction allows the cardiac rhythm management system to adjust the energy level of pace pulses to correspond to a suitable energy expenditure that reliably produces capture. Further, capture detection allows the cardiac rhythm management system to initiate a back-up pulse at a higher energy level whenever a pace pulse does not produce a contraction.

A fusion beat is a cardiac contraction that occurs when two cardiac depolarizations of a particular chamber, but from separate initiation sites, merge. At times, a depolarization initiated by a pacing pulse can merge with an intrinsic beat, producing a fusion beat. Fusion beats, as seen on electrocardiographic recordings, exhibit various morphologies. The merging depolarizations of a fusion beat generally do not contribute evenly to the total depolarization.

Pseudo-fusion occurs when a pacing stimulus is delivered on a spontaneous P wave during atrial pacing or on a spontaneous QRS complex during ventricular pacing. In pseudo-fusion, the pacing stimulus may be ineffective because the tissue around the electrode has already spontaneously depolarized and is in its refractory period.

Pacing therapy can also be used in the treatment of heart failure, which refers to a clinical syndrome in which an abnormality of cardiac function causes a below normal cardiac output that can fall below a level adequate to meet the metabolic demand of peripheral tissues. When uncompensated, it usually presents as congestive heart failure due to the accompanying venous and pulmonary congestion. Heart failure can be due to a variety of etiologies with ischemic heart disease being the most common. It has been shown that some heart failure patients suffer from intraventricular and/or interventricular conduction defects (e.g., bundle branch blocks) such that their cardiac outputs can be increased by improving the synchronization of ventricular contractions with electrical stimulation. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, the most common form of CRT applies stimulation pulses to both ventricles, either simultaneously or separated by a specified biventricular offset interval, and after a specified atrio-ventricular delay interval with respect to the detection of an intrinsic atrial contraction and/or an atrial pace. Appropriate specification of these pacing parameters is necessary in order to achieve optimum improvement in cardiac function.

OVERVIEW

Capture detection can involve discriminating pace-captured beats from fusion/pseudo-fusion beats, intrinsic beats, noise, and noncapture. Discriminating between various cardiac responses can be accomplished by comparing cardiac signals to templates representative of various response types. The present devices and techniques can use templates to recognize or classify various cardiac responses.

The present devices and techniques can involve providing physicians or other users with the ability to quickly visualize and analyze how a patient's cardiac rhythm management (CRM) system or device has been functioning over an extended period of time. This can involve various cardiac devices and methods that can use cardiac waveform classification, generation of related statistics, and display of at least the statistics generated over a period of time. This can include displaying to a physician one or more statistics depicting how a patient's CRM device has been functioning since the patient's last office visit.

In Example 1, a cardiac rhythm management system includes an implantable physiological data monitor, a processor, a memory, and a display. The implantable physiological data monitor is configured to monitor a plurality of cardiac responses. The processor is configured to classify the cardiac response into one of at least three classes including pace-dominant, fusion, and pseudo-fusion. The processor is also configured to calculate statistical information regarding the classified cardiac responses. In this example, the pace-dominant, fusion, and pseudo-fusion classes correspond to a cardiac response resulting from a corresponding electrostimulation. The memory is configured to store the classified cardiac responses and calculated statistical information for future use by the processor or for display. The display is configured to display the statistical information stored in the memory.

In Example 2, the processor of Example 1 further configured to use at least one of the cardiac responses stored in the memory to control a parameter of the implantable cardiac rhythm management device.

In Example 3, the processor of any one of the Examples 1-2 can be configured to use a series of cardiac responses stored in the memory to control a parameter of the implantable cardiac rhythm management device.

In Example 4, the processor of any one of the Examples 1-3 can be configured to use the statistical information about the cardiac responses stored in the memory to control a parameter of the implantable cardiac rhythm management device.

In Example 5, the processor of any one of the Examples 1-4 can be configured to use the statistical information about the cardiac responses stored in the memory to provide programming recommendations. In this example, the display can be configured to display the programming recommendations.

In Example 6, the cardiac rhythm management system of any one of the Examples 1-5 includes an external programming device. In this example, the processor can be configured to use the statistical information about the cardiac responses stored in the memory to send an alert to the external programming device.

In Example 7, the implantable physiological data monitor of any one of the Examples 1-6 is configured to monitor a second physiological parameter and the memory is also configured to store the second physiological data parameter. In this example, the processor can be configured to correlate the calculated statistical information with the second physiological parameter and the results can be displayed in a graphical format.

In Example 8, the cardiac responses of any one of the Examples 1-7 can be measured using electrograms each electrogram including a depolarization.

In Example 9, the implantable physiological data monitor of Example 8 can be configured to monitor a plurality of sensed intrinsic depolarizations and a plurality of evoked response depolarizations. In this example, the processor can be configured to classify the plurality of sensed intrinsic depolarizations and the plurality of evoked response depolarizations and calculate statistical information about the plurality of classified depolarizations. The memory can also be configured to store at least the statistical information about the plurality of classified depolarizations.

In Example 10, the processor of Example 9 can be further configured to automatically use the statistical information about the classifications stored in the memory to control a parameter of the implantable cardiac rhythm management device.

In Example 11, the physiological data monitor of any one of Examples 9-10 can be configured to monitor a second physiological parameter. In this example, the memory can also be configured to store the second physiological parameter. Additionally, the external computing device can be configured to correlate the statistics with the second physiological parameter and display the results in a graphical format.

In Example 12, the processor of any one of Examples 9-11 can be configured to classify the depolarizations according to at least one of heart chamber, right versus left side of heart, or atrial versus ventricular heart chamber.

In Example 13, the processor of any one of Examples 9-12 can be further configured to classify the depolarizations by comparing the depolarization morphology to a template stored in the memory, wherein the stored template enables discrimination between classes.

In Example 14, a method includes monitoring a plurality of cardiac responses, classifying the cardiac responses, calculating statistical information about the classifications, and displaying the statistical information. The monitoring can be accomplished using an implantable cardiac rhythm management device. The classifying can be accomplished using a processor. The cardiac responses can be classified into three classes including pace-dominant, fusion, and pseudo-fusion classes. Pace-dominant, fusion, and pseudo-fusion classes correspond to a cardiac response resulting from a corresponding electrostimulation. The displaying the statistical information regarding the classifications can be on an external device.

In Example 15, the method of Example 14 can include programming a parameter of the implantable cardiac rhythm management device using the statistical information about the cardiac responses.

In Example 16, the calculating of any one of Examples 14-15 can include trending the statistical information over an interval of time.

In Example 17, the interval of time of Example 16 can be an interval of time long enough to allow for monitoring, classifying and calculating over a period of time representative of a chronic condition.

In Example 18, the displaying of any one of Examples 14-17 can include numeric displays and graphical displays.

In Example 19, the monitoring a plurality of cardiac responses of any one of Examples 14-18 can include collecting electrograms associated with each cardiac response, wherein each electrogram includes a depolarization.

In Example 20, the monitoring of Example 19 comprises monitoring a plurality of sensed intrinsic depolarizations and a plurality of evoked response depolarizations. In this example, the classifying also comprises classifying the plurality of sensed intrinsic depolarizations and the plurality of evoked response depolarizations. The calculating statistical information includes calculations about all the classifications.

In Example 21, the classifying the depolarizations of Example 19 includes classifying according to at least one of heart chamber, right versus left side of heart, or atrial versus ventricular heart chamber.

In Example 22, the classifying the depolarizations of any of the Examples 19-21 includes comparing each depolarization morphology to a stored template, where the stored template enables discrimination between the classes.

In Example 23, the classifying the depolarizations of any of the Examples 19-21 includes comparing a depolarization morphology to a plurality of stored templates, wherein each stored template enables identification of one or more of the classes.

In Example 24, the method of any one of Examples 14-23 includes automatically programming a parameter of the implantable cardiac rhythm management device using the classification information.

In Example 25, the method of any one of Examples 14-23 includes automatically programming a parameter of the implantable cardiac rhythm management device using the calculated statistical information. In this example, the programmed parameter can be displayed in association with the calculated statistical information used to program the parameter.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
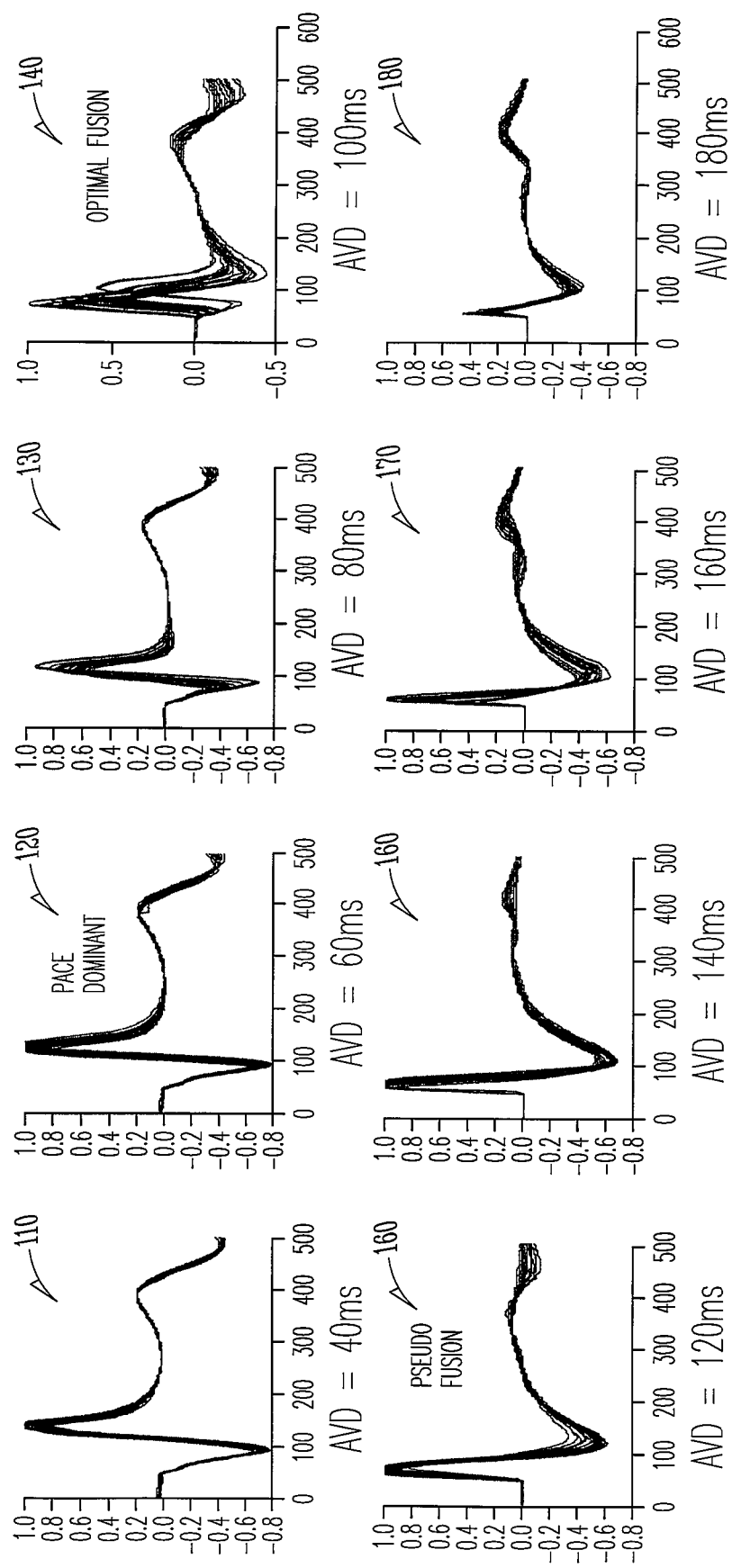
FIG. 1 is a series of illustrations depicting a plurality of electrograms taken at various atrial-ventricle delay timings.

As described above, cardiac rhythm management systems can provide cardiac resynchronization therapy, such as pacing stimulation applied to one or more heart chambers in a manner that compensates for heart failure conditions or conduction delays. Ventricular resynchronization pacing can be useful in treating heart failure in patients with interventricular or intraventricular conduction defects because, although not directly inotropic, resynchronization can result in a more coordinated contraction of the ventricles, improving pumping efficiency and increasing cardiac output. Ventricular resynchronization can be achieved in certain patients by pacing at a single non-typical site, such as the left ventricle instead of the right ventricle in patients with left ventricular conduction defects. Resynchronization pacing can also involve bi-ventricular pacing with the paces to right and left ventricles delivered either simultaneously or sequentially, with the interval between the paces termed the VV delay (VVD) interval (also sometimes referred to as the LV offset (LVO) interval or biventricular offset (BVO) interval). The VV delay interval can be zero to pace both ventricles simultaneously or non-zero to pace the left and right ventricles sequentially. A negative VVD can be used to refer to pacing the left ventricle before the right, while a positive VVD can be used to refer to pacing the right ventricle first.

Cardiac resynchronization therapy can be conveniently delivered in conjunction with a bradycardia pacing mode. Bradycardia pacing modes refer to pacing techniques used to pace the atria or ventricles in a manner that enforces a certain minimum heart rate. Because of the risk of inducing an arrhythmia with asynchronous pacing, pacemakers for treating bradycardia can be programmed to operate synchronously in a so-called demand mode, such as in which sensed cardiac events occurring within a defined interval either trigger or inhibit a pacing pulse. Inhibited demand pacing modes can use escape intervals such as to control pacing in accordance with sensed intrinsic activity. In an inhibited demand mode, a pacing pulse can be delivered to a heart chamber during a cardiac cycle only after expiration of a defined escape interval during which no intrinsic beat by the chamber is detected. For example, a ventricular escape interval for pacing the ventricles can be defined between ventricular events, referred to as the cardiac cycle (CC) interval with its inverse being the lower rate limit or LRL. The CC interval is restarted with each ventricular sense or pace. In atrial tracking and AV sequential pacing modes, another ventricular escape interval is defined between atrial and ventricular events, referred to as the AV delay (AVD) interval, where a ventricular pacing pulse is delivered upon expiration of the AV delay interval if no ventricular sense occurs before. In an atrial tracking mode, the atrio-ventricular pacing delay interval is triggered by an atrial sense and stopped by a ventricular sense or pace. An atrial escape interval can also be defined for pacing the atria either alone or in addition to pacing the ventricles. In an AV sequential pacing mode, the atrio-ventricular delay interval is triggered by an atrial pace and stopped by a ventricular sense or pace. Atrial tracking and AV sequential pacing can be combined so that an AVD interval starts with either an atrial pace or sense. For biventricular pacing, the AVD interval refers to the interval between an atrial event (e.g., a pace or sense in one of the atria, usually the right atrium) and the first ventricular pace which pre-excites one of the ventricles. The pacing instant for the non-pre-excited ventricle can be specified by the VVD interval so that it is paced at an interval AVD+VVD after the atrial event. With either biventricular or left ventricle-only pacing, the AVD interval can be the same or different depending upon whether it is initiated by an atrial sense or pace (e.g., in atrial tracking and AV sequential pacing modes, respectively). A way of implementing biventricular pacing or left ventricle-only pacing can be to base the timing upon only right ventricular activity so that ventricular escape intervals are reset or stopped by right ventricular senses.

For good hemodynamic performance, it can be desirable to deliver ventricular pacing, whether for resynchronization pacing or bradycardia pacing, in an atrial tracking or AV sequential pacing mode such as to maintain the function of the atria in pre-loading the ventricles (sometimes referred to atrio-ventricular synchrony). CRT is intended to improve a patient's cardiac pumping function, so it is therefore normally delivered in an atrial-tracking and/or AV sequential mode and involves specification of an AVD interval (and, in the case of biventricular pacing, a VVD interval) which, ideally, results in the ventricles being synchronized during systole after being optimally preloaded during atrial systole. In this way, both optimal interventricular synchrony and optimal atrio-ventricular synchrony can be achieved.

Cardiac resynchronization therapy can be used to treat patients with heart failure due to left ventricular dysfunction, which can be either caused by or contributed to by left ventricular conduction abnormalities such as left bundle branch block. (More rarely, some patients have a right ventricular conduction deficit such as right bundle branch block and can benefit from pre-excitation of the right ventricle such as to achieve synchronization of their ventricular contractions.) In patients with a left ventricular conduction deficit, the left ventricle or parts of the left ventricle contract later than normal during systole which thereby impairs pumping efficiency. To resynchronize ventricular contractions in such patients, pacing therapy can be applied such that the left ventricle or a portion of the left ventricle can be pre-excited relative to when it would become depolarized in an intrinsic contraction. Optimal pre-excitation of the left ventricle in a given patient can be obtained with biventricular pacing or with left ventricular-only pacing by pre-exciting the left ventricle with a pace delivered to the left ventricle which excites the left ventricular free wall. The desired situation is simultaneous contraction of the left ventricular free wall and ventricular septum (septum-free wall fusion). The excitation of the ventricular septum can be a result of either intrinsic activation from the AV node or a pace delivered to the right ventricle. If intrinsic AV conduction to the right ventricle is normal, intrinsic activation of the ventricular septum occurs at an interval following an atrial contraction which produces optimal pre-loading of the ventricles during atrial systole. Therefore, in a patient with normal intrinsic AV conduction to the right ventricle but with a left ventricular conduction deficit, the hemodynamically optimum AVD interval for pre-exciting the left ventricle is one which results in the left ventricular free wall contracting due to the pace at the same time that the ventricular septum is contracting due to intrinsic activation. This situation can be brought about by pre-exciting the left ventricle at the optimum AVD interval with either left ventricle-only or biventricular pacing. In the latter case, depending upon the implementation, the right ventricular pace scheduled to occur at the VVD interval following expiration of the AVD interval can either be inhibited by the intrinsic right ventricular activation, occur coincidentally with the right ventricular activation, or occur after intrinsic right ventricular activation during the refractory period.

In the case of a patient without intact intrinsic AV conduction, left ventricle-only pacing would produce a ventricular contraction in which depolarization spreads only from the left ventricular pacing site. It may therefore be desirable to deliver paces to both ventricles in a biventricular pacing mode in order to produce a more hemodynamically effective contraction. The minimum pacing rate would normally then be set to a value which results in only paced cycles. That is, any intrinsic activation due to an idioventricular rhythm would occur at too slow a rate to inhibit paces. The AV delay and VV delay intervals are then set to values which provide atrio-ventricular and interventricular synchrony. If, however, the patient does not have complete AV block, such that intrinsic activation of either ventricle may occur intermittently, it can be desirable to utilize biventricular pacing and to set the AV delay and VV delay intervals to values which produce fusion beats when intrinsic conduction to the ventricles occurs. For example, in a patient with a left ventricular conduction deficit and intermittent AV block to the right ventricle, pre-excitation of the left ventricle with an optimum AV delay intervals would produce a fusion beat when intrinsic conduction to the right ventricle occurs which results in the left ventricular free wall contracting due to the pace at the same time that the ventricular septum is contracting due to intrinsic activation. The optimum VV delay in this case would then be a value long enough to so that the right ventricular pace subsequent to the left ventricular pace is inhibited by the intrinsic right ventricular activation (or is delivered when the right ventricle is refractory) but short enough to produce a hemodynamically effect beat when no intrinsic AV conduction to the right ventricle occurs.

As discussed above, in a patient with normal intrinsic AV conduction to the right ventricle and a left ventricular conduction deficit, the desired result of CRT is a fusion beat such that the left ventricular pace causes contraction of the left ventricular free wall at the same time intrinsic conduction from the AV node causes contraction of the ventricular septum. Such a fusion beat can be recognized in an evoked response electrogram. An electrogram is a signal showing the amplitude and time course of cardiac depolarization and repolarization as recorded by either internal or external electrodes, the latter referred to as a surface EKG. An evoked response electrogram is one recorded during a paced cardiac cycle. Since the depolarization and repolarization patterns in the ventricles are different for paced and intrinsic activation, electrograms recorded during paced, intrinsically activated, and fusion beats are morphologically distinguishable. In some examples, intrinsic activation can be referred to as sensed.

The proper programming of a CRM device can be enhanced by providing a physician greater insights into the operation of the CRM device within a specific patient over a period of time, such as a chronic period of time between outpatient office visits. This can be compared to an approach to programming CRM devices based on limited information provided by acute measurements or one-time tests performed in the physician's office. In a sophisticated CRM device that includes some ability to automatically adapt a parameter such as AV delay or VV delay, parameters programmed by the physician's can limit such closed-loop automatic adaptations. Therefore, it is helpful to provide good information for making programming choices, such as by providing chronic rather than acute patient information.

A recent study published in the Journal of the American College of Cardiology (The Utility of 12-Lead Holter Monitoring in Patients with Permanent Atrial Fibrillation for the Identification of Nonresponders after Cardiac Resynchronization Therapy, JACC Vol. 53, No. 12, 2009 Mar. 24, 2009) demonstrates the potential importance of detailed information related to paced, fusion and pseudo-fusion statistics. The study evaluated 19 patients with atrial fibrillation (AF) and HF in the setting of ventricular dysfunction. The study determined that the percentage of ventricular pacing is an inadequate indicator of adequate bi-ventricular pacing, due to the relatively high percentages of fusion and pseudo-fusion beats. According to the study, CRT patients with a high percentage of pseudo-fusion beats do not tend to respond clinically. Thus, providing physicians with detailed statistical information regarding the presence of paced, fusion and pseudo-fusion beats in patients with AF and HF has been shown to be beneficial.

While the following examples focus on atrioventricular (AV) delay timings as one parameter that can be optimized using the described techniques, the described fusion statistics can also be useful in visualizing and optimizing other CRM device functions, as noted above. For example, in CRT the application of a bi-ventricular trigger in a non-tracking mode for patients with no AV conduction issues can be optimized using fusion statistics. Making the detailed statistics described below available to physicians can allow for better application of CRT to treat dysyncrony that adversely affects cardiac output.

Figure 2:
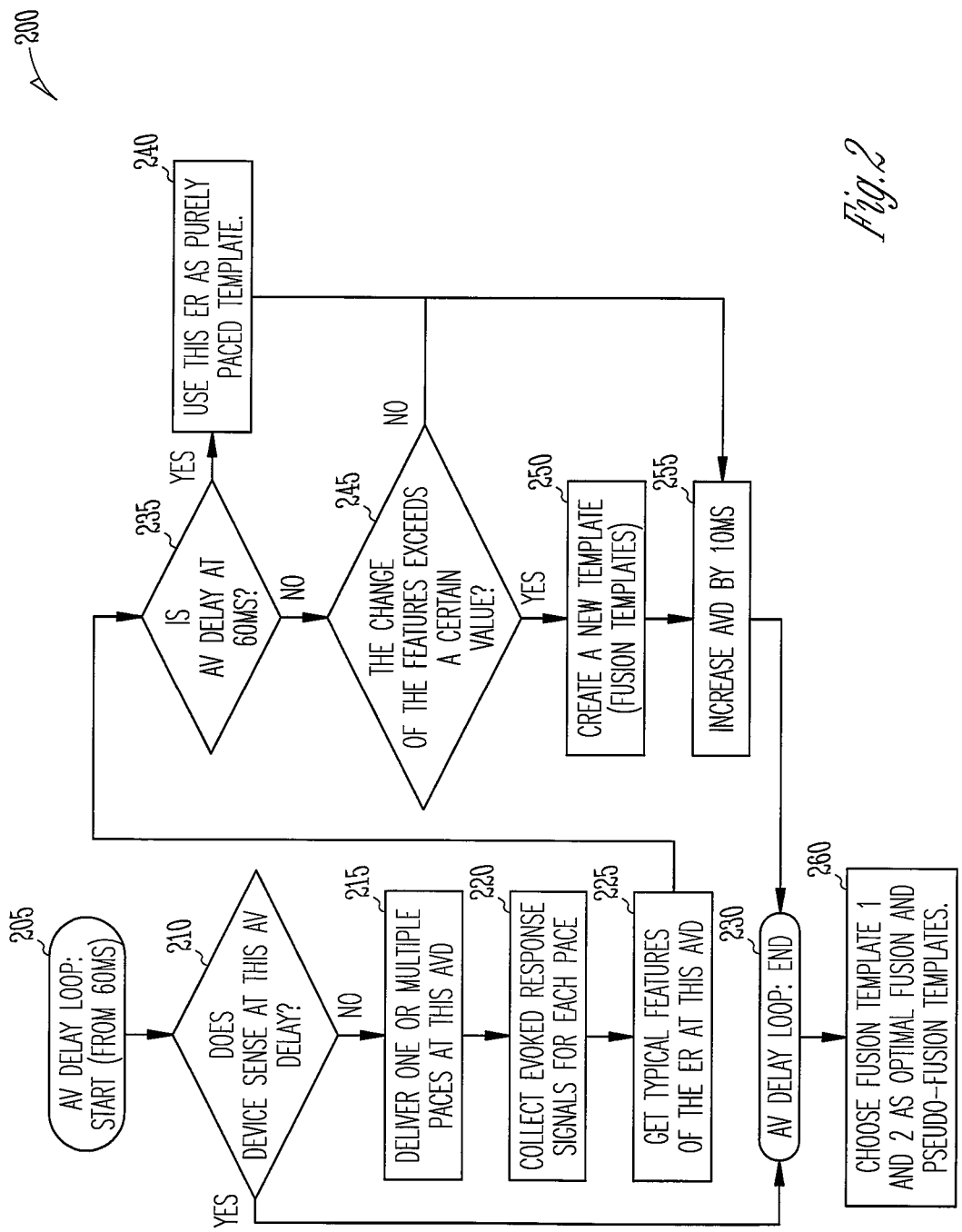
FIG. 2 is a flowchart illustrating an example of a technique for creating evoked response templates which can be used to classify individual evoked responses.

FIG. 1 is a series of illustrations depicting a plurality of electrograms taken at various atrioventricular (AV) delay timings. Each of the eight illustrations depicts a series of evoked response electrograms at a specific AV delay. For example, graph 120 illustrates a series of electrograms at a 60 ms AV delay. The electrograms illustrated in graph 120 demonstrate an example of a pace dominant morphology. A heart beat can produce an electrogram that exhibits pace dominant morphology when a pacing stimulus produces a contraction in the heart tissue. Extending the AV delay to 100 ms, as shown in graph 140, the collected electrograms depict an example of fusion morphology. A heart beat can produce an electrogram that exhibits fusion morphology when a cardiac contraction occurs when two cardiac depolarizations of a particular chamber, but from separate initiation sites, merge. Further extending the AV delay to 120 ms, shown in graph 150, depicts electrograms that exhibit a pseudo-fusion morphology. A heart beat can produce an electrogram that exhibits pseudo-fusion morphology when a pacing stimulus is delivered on a spontaneous P wave during atrial pacing or on a spontaneous QRS complex during ventricular pacing. These different electrogram morphologies can be used to create morphology templates. An example technique for creating morphology templates is depicted in FIG. 2. Further details on an example of morphology template creation can be found in U.S. patent application Ser. No. 11/116,544, by Meyer et al., entitled "CARDIAC SIGNAL TEMPLATE GENERATION USING WAVEFORM CLUSTERING," filed on Apr. 28, 2005, which has been incorporated by reference into this application.

Figure 3:
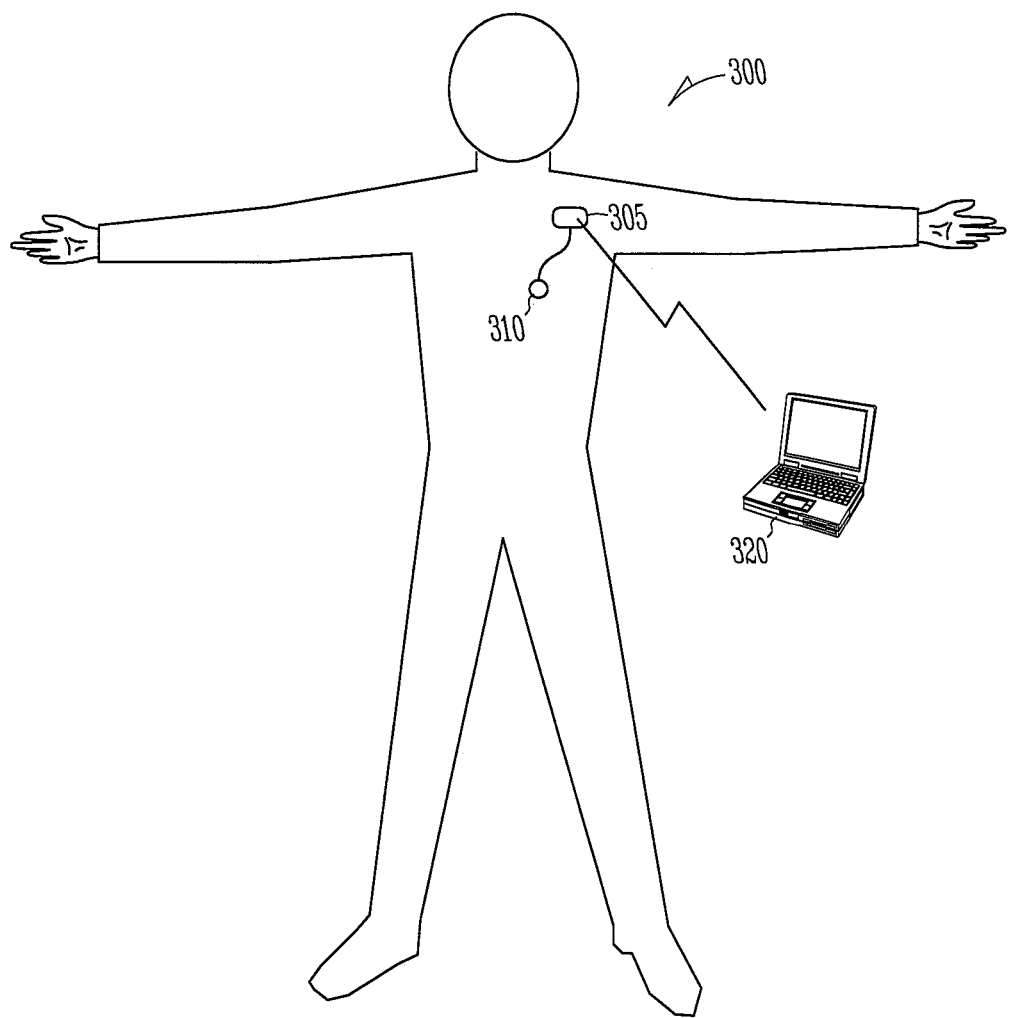
FIG. 3 is a block diagram illustrating an example of an implantable cardiac rhythm management system communicatively coupled to an external programming and diagnostic device.

FIG. 3 is a block diagram illustrating an example of an implantable cardiac rhythm management system communicatively coupled to an external programming and diagnostic device. The system 300 can include an implantable medical device (IMD) 305, a physiological data sensor 310, and an external device 320. In an example, the IMD 305 can include a cardiac rhythm management (CRM) device used to provide cardiac rhythm management therapy to a patient's heart (such as described above). In an example, the physiological data sensor 310 can be used to detect an electrogram including evoked response depolarization information. In an example, the physiological data sensor 310 can additionally or alternatively be used to monitor one or more other physiological parameters of a cardiovascular nature, such as heart rate, heart sound, respiration rate, or blood pressure, cardiac activation sequence, among others. In some examples, multiple physiological data monitors can be employed to monitor multiple relevant physiological parameters.

The external device 320 can be used for programming the IMD 305 or displaying data obtained from the IMD. In an example, the external device can include a personal computer, such as a laptop, configured to communicate with the IMD 305. In an example, the external device 320 can communicate via a hardwired communication link with the IMD 305. In an example, the external device 320 can communicate over a wireless communication link with the IMD 305. In an example, the external device 320 can receive data from the IMD 305 and display the received data, such as on a computer display. The external device 320 can also be configured to calculate statistics or perform additional analysis such as to assist a physician, technician, or engineer in adjusting operating parameters of the IMD 305. An example of additional analysis can include correlating various physiological data parameters downloaded from the IMD 305 to statistics gathered by the IMD over a period of time. For example, the external device 320 can correlate respiration rate to statistics concerning evoked response depolarization classifications.

Figure 4:
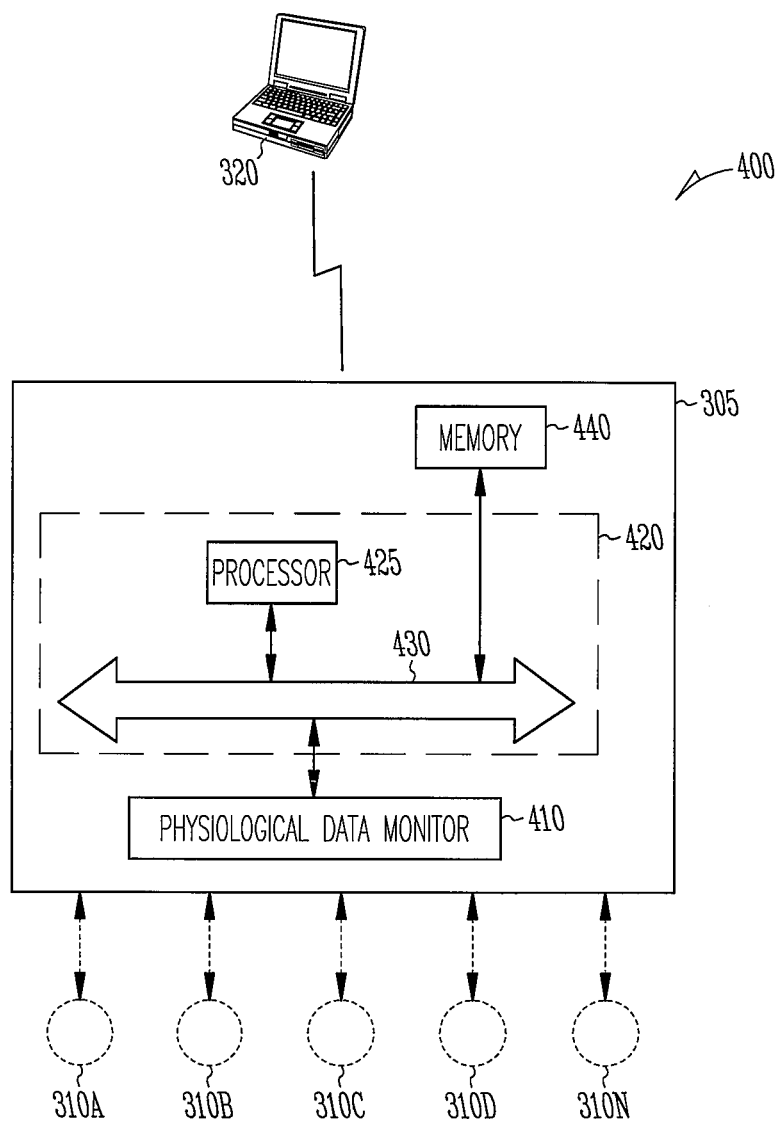
FIG. 4 is a block diagram illustrating an example of an implantable cardiac rhythm management system that can be used for generation and display of fusion statistics.

FIG. 4 is a block diagram illustrating an example of an implantable cardiac rhythm management system that can be used for generating and display of one or more fusion statistics. The system 400 can include an implantable medical device 305, one or more physiological data sensors 310A, 310B, . . . , 310N (collectively hereinafter referred to as 310), and an external device 320. In the system 400, the IMD 305 can include a physiological data monitor 410, a processor 425, a communication bus 430, and a memory 440. In some examples, the processor 425 and the communication bus 430 can be integrated into a processor 420, allowing the physiological data monitor 410 and the memory to communicate directly to the processor 420. In some examples, some of the physiological data sensors 310, can directly communicate with the external device over a communication link.

In an example, the physiological data monitor 410 can receive data from one or more physiological data sensors 310. In certain examples, the physiological data sensors 310 can be sensors implanted within the patient's body, also referred to as internal sensors. In other examples, the physiological data sensors 310 can be sensors adhered to a patient's skin or worn against a patient's skin, or other ambulatory external sensors. In some examples, the physiological data sensors 310 include both external and internal sensors. The monitored physiological data can then be transferred to the processor 425 or stored directly in the memory 440. The memory 440 can be accessible to the external device 320 such as over a communication link. As discussed above, the communication link between the external device 320 and the IMD 305 can be either wired or wireless.

Figure 5:
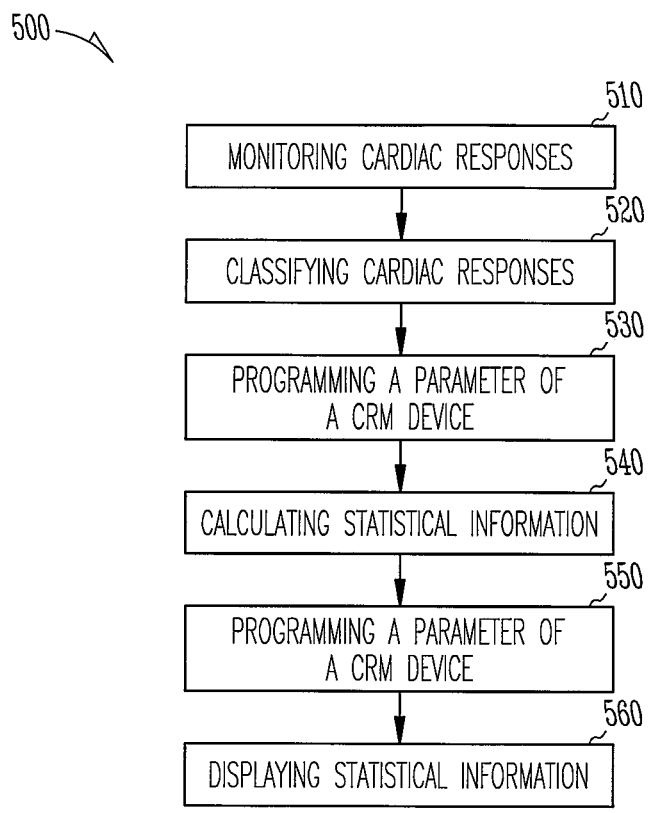
FIG. 5 is a flowchart illustrating an example of a method of generating and displaying fusion statistics.

FIG. 5 is a flowchart illustrating an example of a method of generating and displaying one or more fusion statistics. In this example, a method 500 details a series of operations for generating and displaying statistics related to classified cardiac responses monitored and collected by an TMD 305. The method 500 includes monitoring cardiac responses 510, classifying cardiac responses 520, calculating statistical information 540, and displaying statistical information 560. In certain examples, the method 500 also includes an operation for programming one or more parameters of an TMD 305 at either 530 or 550. In some examples, the IMD 305 can be a cardiac rhythm management (CRM) device, as indicated by 530 and 550. The following example focuses on monitoring and classifying electrograms as the method of measuring the cardiac response. As is discussed further below, there are a variety of methods for measuring cardiac responses, such as electrograms, cardiac activation sequence, or other physiological sensors.

In an example, the method 500 can begin by monitoring one or more electrograms at 510 such as by using the physiological data monitor 410 within the IMD 305. As discussed above, the physiological data monitor 410 can receive electrogram data from either one or more internal sensors 310 or one or more external sensors 310 (where the external sensors provide a surface EKG). In either an internal or external configuration, the physiological data sensors can provide electrogram data, including depolarization information, to the data monitor 410. Once an electrogram has been monitored, the method 500 continues by classifying the depolarization at 520. In an example, classifying a depolarization can be done by the processor 425. At 520, the processor 425 classifies the depolarization into only one of at least three classes including pace-dominant, fusion, and pseudo-fusion. As discussed above, pace-dominant, fusion, and pseudo-fusion classes correspond to an evoked response depolarization resulting from an electrostimulation (e.g., pacing pulse). An example of a method of classification is described below in relation to FIGS. 6 and 7. Examples of detailed methods of classification are also described in U.S. patent application Ser. No. 11/116,544, by Meyer et al., entitled "CARDIAC SIGNAL TEMPLATE GENERATION USING WAVEFORM CLUSTERING," filed on Apr. 28, 2005, which has been incorporated by reference into this application.

Figure 8A:
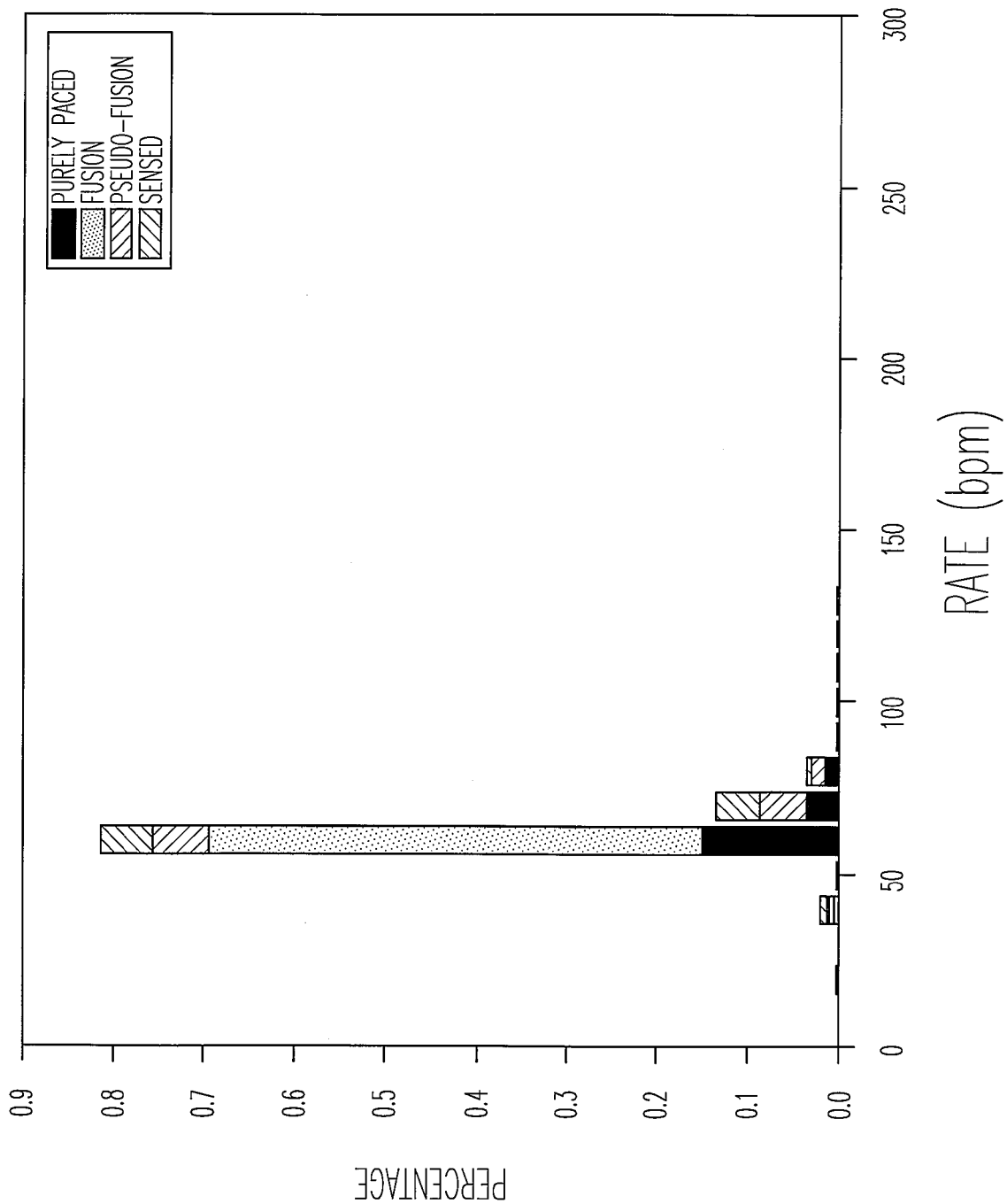
FIGS. 8A-8D are illustrations depicting examples of graphical displays of fusion statistics.

The method 500 continues at 540 by calculating statistical information associated with the classified depolarizations and in some examples with other monitored physiological data. In an example, the processor 425 updates one or more statistical counters as the depolarizations are classified. As the depolarizations are classified at 520, the processor 425 can maintain running totals for each classification, an example is shown below in Table 1. Table 1 depicts an example focused on right ventricular pacing. From the running totals, statistics such as percent of total can be calculated and displayed. In an example, the running totals can be displayed in association with another physiological data parameter monitored by the data monitor 410, such as heart rate. FIG. 8A depicts an example of classified depolarizations plotted on a histogram according to heart rate in beats per minute. In an example, similar data could be correlated to respiration rate or monitored blood pressure, among other things. Multidimensional statistical correlations may be calculated, for example, between the classified depolarizations, heart rate, and respiration rate. The correlation to other monitored physiological parameters can be particularly useful in providing context for the statistics, such as when reviewed by a treating physician.

TABLE 1

| Right Ventricular Counters: | | |
|---|---|---|
|  | Percentage | Count |
| Paced: | 80% | 10,000,000 |
| Pace-Dominate | 40% | 5,000,000 |
| Fusion | 24% | 3,000,000 |
| Pseudo-Fusion | 16% | 2,000,000 |
| Sensed | 20% | 2,500,000 |

In an example, the processor 425 can be configured to calculate trend data related to the classified depolarizations over a specified time period, such as chronically between typically-scheduled outpatient doctor visits. In another example, the external device 320 can be configured to calculate and maintain trend data over a specified time period. In either example, the time period typically represents an extended period of time, such as a week or month. In an example, the time period extends over the period of time between office visits. The time period can be configured by the physician to meet specific diagnostic needs related to optimizing configuration of a patient's IMD.

In an example, the processor 425 can be configured to keep running totals broken out into greater detail regarding sensed versus paced as well as chambers of the heart, such as right and left ventricle or right atrium. Table 2 depicts an example of more detailed totals for ventricular counters. This table can be further broken out for Atrial Paced or Atrial Sensed for each category.

TABLE 2

| Ventricle Counters | Percentage | Count |
|---|---|---|
| Sensed | 1.00% | 105,851 |
| RV Paced, LV Sensed | 1.00% | 105,851 |
| RV Sensed, LV Paced | 2.00% | 211,703 |
| Paced-Dominant | 1.00% | 105,851 |
| Fusion | 0.50% | 52,926 |
| Pseudo-fusion | 0.50% | 52,926 |
| RV Paced, LV Paced | 96.00% | 10,161,734 |
| Paced-Dominant | 80.00% | 8,468,112 |
| Fusion | 10.00% | 1,058,514 |
| Pseudo-fusion | 6.00% | 635,108 |
|  |  | 10,585,140 |

In an example, the statistics calculated at 540 can include multivariable analysis involving other monitored physiological parameters, such as heart rate, respiration rate, blood pressure, or even posture. These additional physiological parameters can affect the incidence of the various evoked and sensed responses and the associated morphologies. In some examples, a calculation can be performed to estimate oxygen delivery rate, which depends on breathing and blood flow. In this example, blood flow can be represented by heart rate and a measure of pumping efficiency. The measure of pumping efficiency can be derived from the sensed and evoked response morphologies represented in the calculated statistics. Using these variables, both a graphical and numeric display can be generated to provide a physician with valuable information related to the performance of a patient's CRM device.

In an example, the method 500 continues at 560 by displaying the statistical information calculated at 540. Displaying statistical information can be done by the external device 320. In certain examples, statistical information can be displayed both graphically and numerically on the external device's 320 computer screen. In other examples, the statistical information can be displayed through print outs generated by the external device 320. In some examples, the external device 320 can display the statistical information on screen or provide printed copies on demand. In an example, the external device 320 can be used to communicate the statistical information, as well as any raw data downloaded from the IMD 305, to other devices through electronic messaging or some similar electronic transmission mechanism.

In some examples, either classified depolarization data or statistical information can be used to program a parameter of the IMD 305. At 530, one or more classified depolarizations can be used by the processor 425 to program or re-program an operating parameter of the IMD. For example, the processor 425 within a CRM device can modify the AV delay timing based on one or more classified depolarizations. In another example, the processor 425 within a CRM device can modify the AV delay timing based on calculated statistical information, at 550. In this example, the processor 425 can be configured to reduce the AV delay if the statistical information indicates that over a certain percentage of the depolarizations are being classified as pseudo-fusion. The adjustment of the programming parameters can also be conducted in a real-time basis under certain physiological conditions. For example, if under certain heart rate and respiration rate, over a certain percentage of the depolarizations are observed, the AV delay can be adjusted if a particular heart rate and respiration rate are reached.

Figure 6:
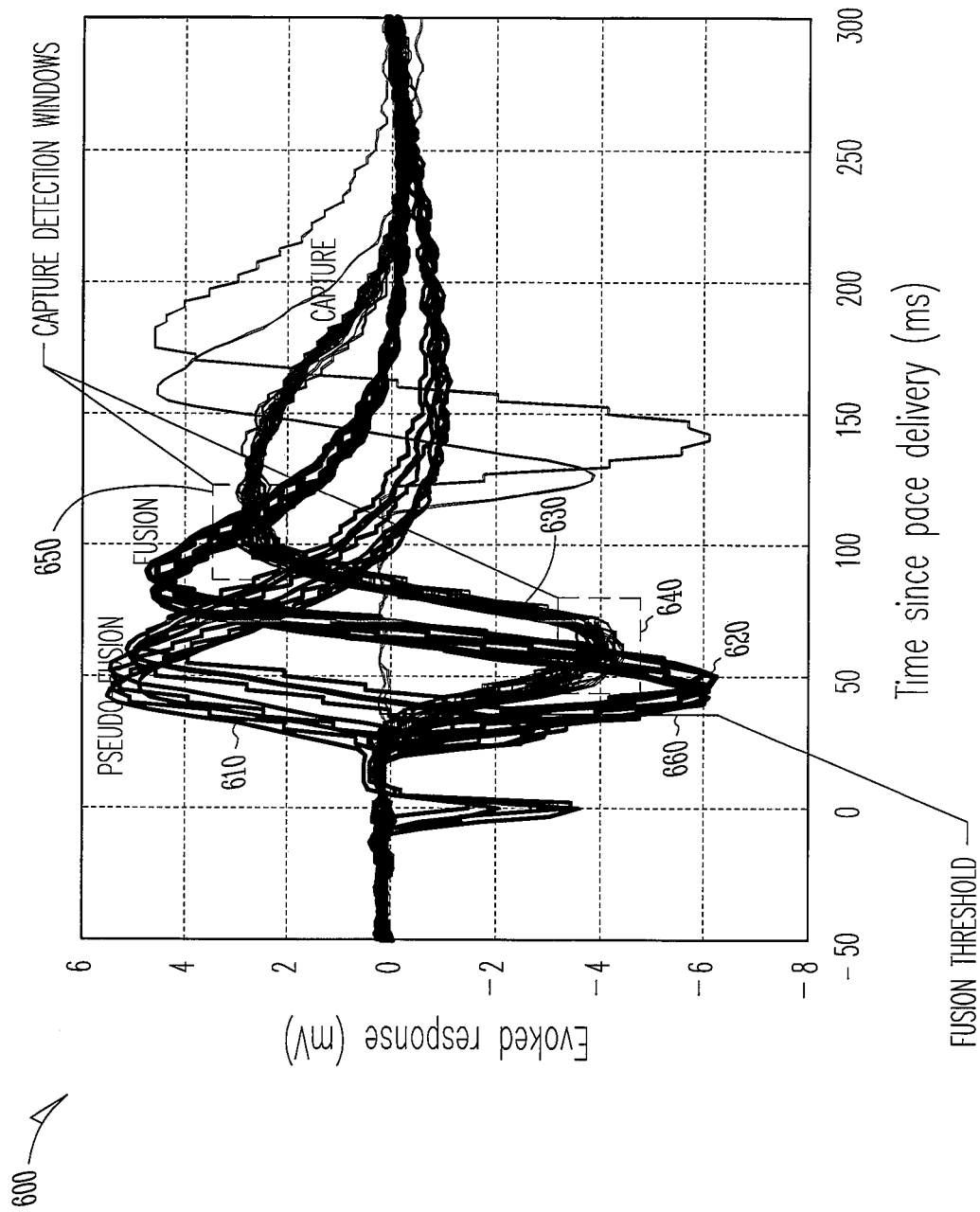
FIG. 6 is an illustration depicting various evoked responses demonstrating capture, fusion, and pseudo-fusion pacing conditions.

FIG. 6 is an illustration depicting various evoked responses demonstrating capture, fusion and pseudo-fusion pacing conditions. FIG. 6 includes a series of capture (pace-dominate) depolarizations 630, a series of fusion depolarizations 620, and a series of pseudo-fusion depolarizations 610. Plotting the depolarizations together highlights the different morphologies represented by the different classifications. FIG. 6 also illustrates detection windows 640, 650 used in some examples to discriminate between the different classifications. These detection windows 640, 650 are used within a method 700, which depicts an example method of classification. Finally, FIG. 6 also includes a pseudo-fusion threshold 660, which can be used in an example to discriminate between fusion and pseudo-fusion depolarizations.

Figure 7:
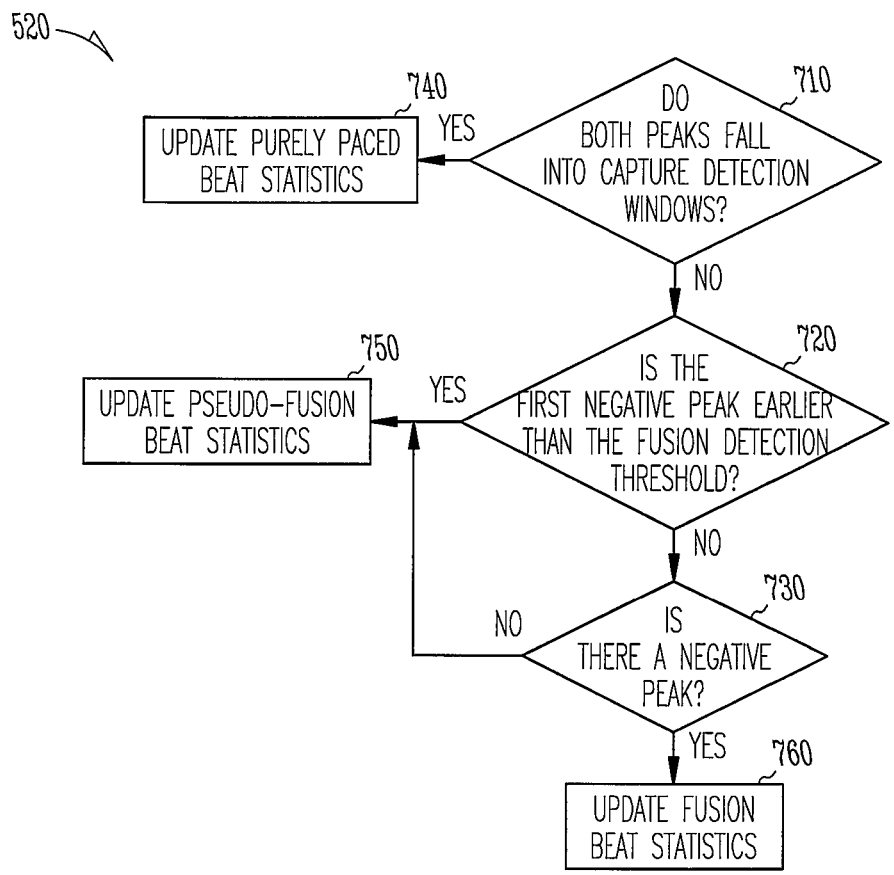
FIG. 7 is a flowchart illustrating an example of a technique for classifying evoked responses using capture detection windows.

As mentioned above, FIG. 7 is a flowchart illustrating an example of a technique for classifying evoked responses using capture detection windows. FIG. 7 depicts a detailed example of operations that can be performed at 520 of method 500. The method 520 begins at 710 by determining whether both peaks of the depolarization fall within capture detection windows 640, 650. If the peaks do both fall within capture detection windows, then the depolarization can be classified as a pace-dominant depolarization and the pace-dominant statistics are updated at 740. If the peaks do not both fall within the capture detection windows 640, 650, the method 520 continues at 720. At 720, the method 520 determines whether the first negative peak occurs prior to the pseudo-fusion threshold 660. If the first negative peak does occur prior to the pseudo-fusion threshold 660, the method 520 continues at 750 by updating the pseudo-fusion statistics (and classifying the depolarization as pseudo-fusion). If the first negative peak does not occur prior to the pseudo-fusion threshold 660, then the depolarization can be checked to determine whether it has a negative peak, at 730. If a negative peak exists, then the method 520 classifies the depolarization as fusion and updates the fusion statistics at 760. In this example, if the depolarization does not have a negative peak it can be classified as pseudo-fusion and the pseudo-fusion statistics are updated at 750.

In an example, the classification statistics are stored in a data table structure within the memory 440. In this example, the individual statistic to be maintained can be stored in a separate row, for example Right Ventricle Paced, Left Ventricle Sensed Fusion can be maintained within a row. Each row contains a counter that can be updated each time the processor 425 classifies a depolarization as fitting the row's profile. In another example, the classification statistics are maintained through hardware counters dedicated to each possible classification. In this example, the counters are incremented each time the processor 425 detects an associated depolarization.

In an example device, the number of paced or sensed beats at different heart rates are counted. Table 3 illustrates a simple example of this configuration:

TABLE 3

| Heart Rate (BPM) | Paced | Sensed |
| --- | --- | --- |
| 30-40 | 200 | 10,000 |
| 40-50 | 100,000 | 200,000 |
| ... | ... | ... |
| 240-250 | 0 | 1,000 |

In this example, an external programming device, such as 320, can interrogate the implantable device 305 to set this table and calculate the overall counters. The programming device 320 can then produce output similar to that shown in Table 1. In additional examples, more categories can be configured, adding columns such as Respiration Rate (BPM), Pace Dominant, Fusion and Pseudo-fusion.

FIGS. 8A-8D are illustrations depicting examples of displays of fusion statistics. As discussed above, FIG. 8A is a graph illustrating classified depolarization statistics correlated with heart rate and plotted on a histogram. The illustrated example of data highlights very quickly the presence of a large percentage of fusion depolarizations within a narrow band of heart rate, around 60-70 beats per minute. This graphical representation enables a physician to very quickly gain insight into the operation of the patient's IMD over the plotted range of heart rates. In another example, this same classification data could be plotted against respiration rate or blood pressure, providing additional snapshots of IMD operation.

Figure 8B:
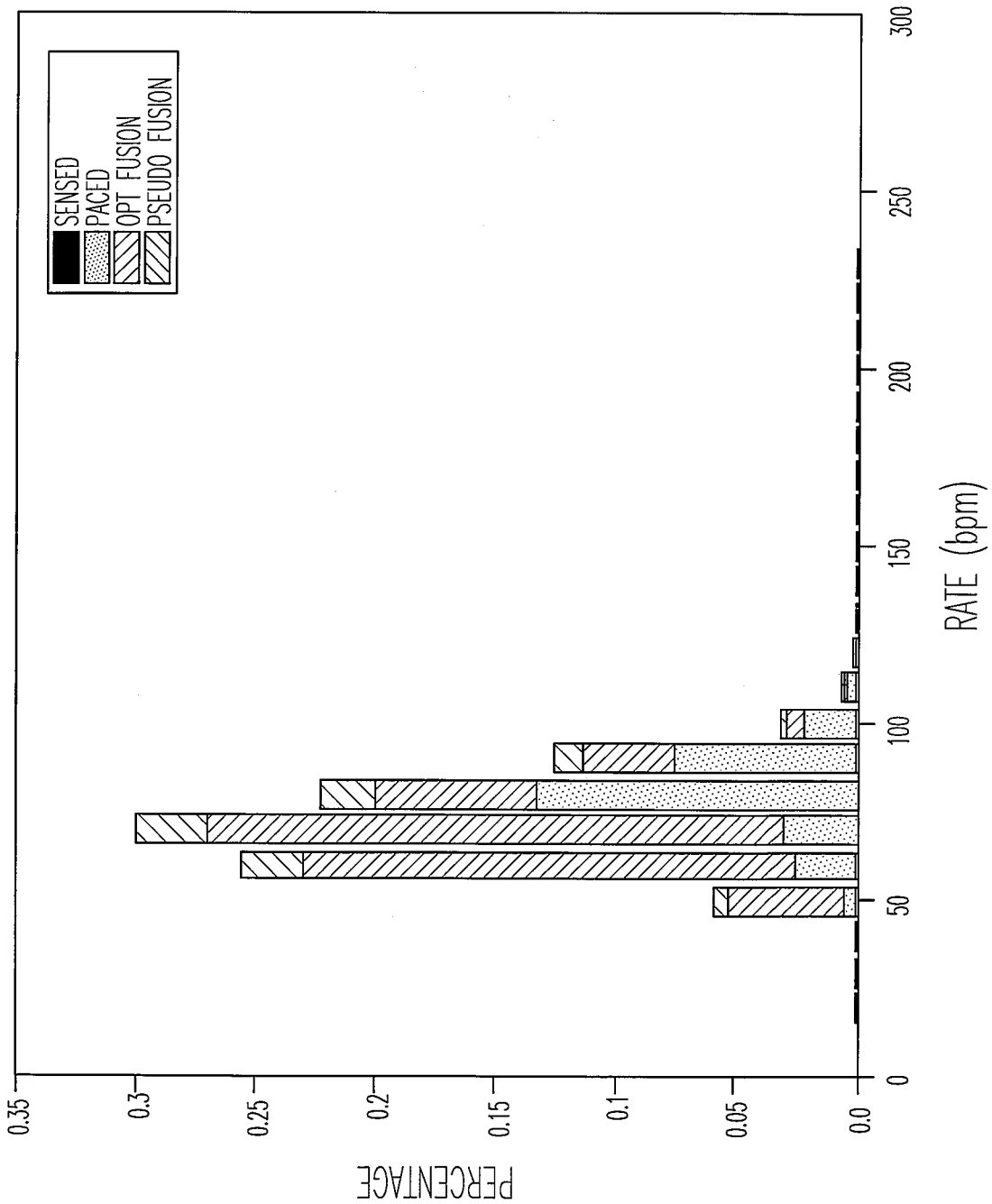
Figure 8C:
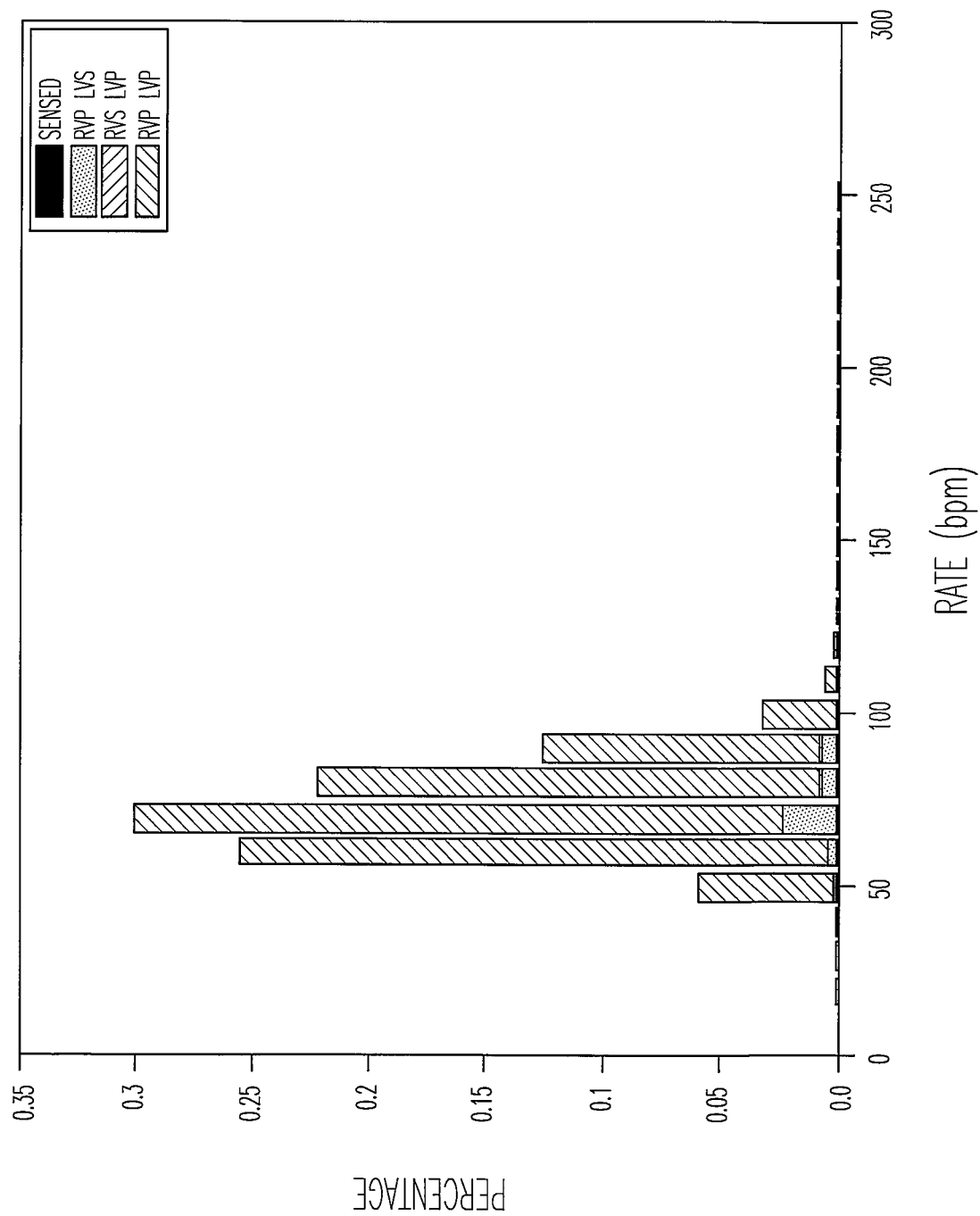
Figure 8D:
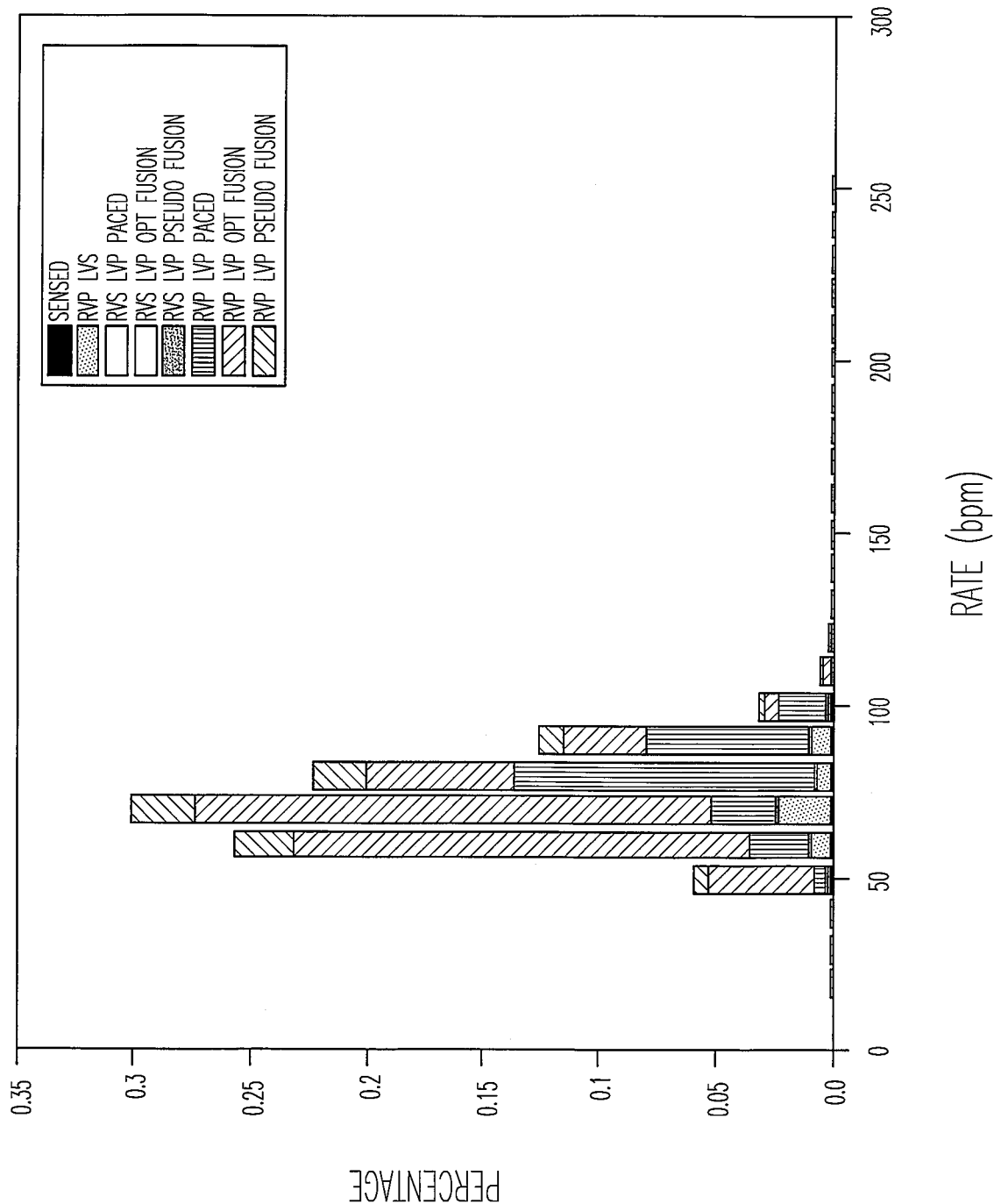

FIGS. 8B-8D are histogram type graphs illustrating additional examples of data correlated to the patient's heart rate. These additional graphs depict various levels of detail from general depolarization classifications, in FIG. 8B, to heart chamber specific depolarization classifications, in FIG. 8D. In an example configuration, the IMD 305 can maintain a level of detail as selected by the physician.

Examples discussed above focus on utilizing electrograms to detect pace dominant, fusion or pseudo-fusion. In additional examples, different physiological sensor measurements can be used to classify the cardiac responses, such as cardiac activation or other physiological sensors. Further details on cardiac activation sequence can be found in U.S. patent application Ser. No. 11/601,216, published as US 2008/0119903, by Arcot-krishnamurthy et al., titled CARDIAC RESYNCHRONIZATION THERAPY OPTIMIZATION USING CARDIAC ACTIVATION SEQUENCE INFORMATION, which is hereby incorporated by reference.

Additional examples of the above subject matter can include other electrical properties of the heart that describe the level of synchrony of the heart, such as evoked response amplitude and width. These additional properties can be trended and displayed in a manner similar to that described above in relation to evoked response and heart rate.

Example External Device and Machine-Readable Medium

Figure 9:
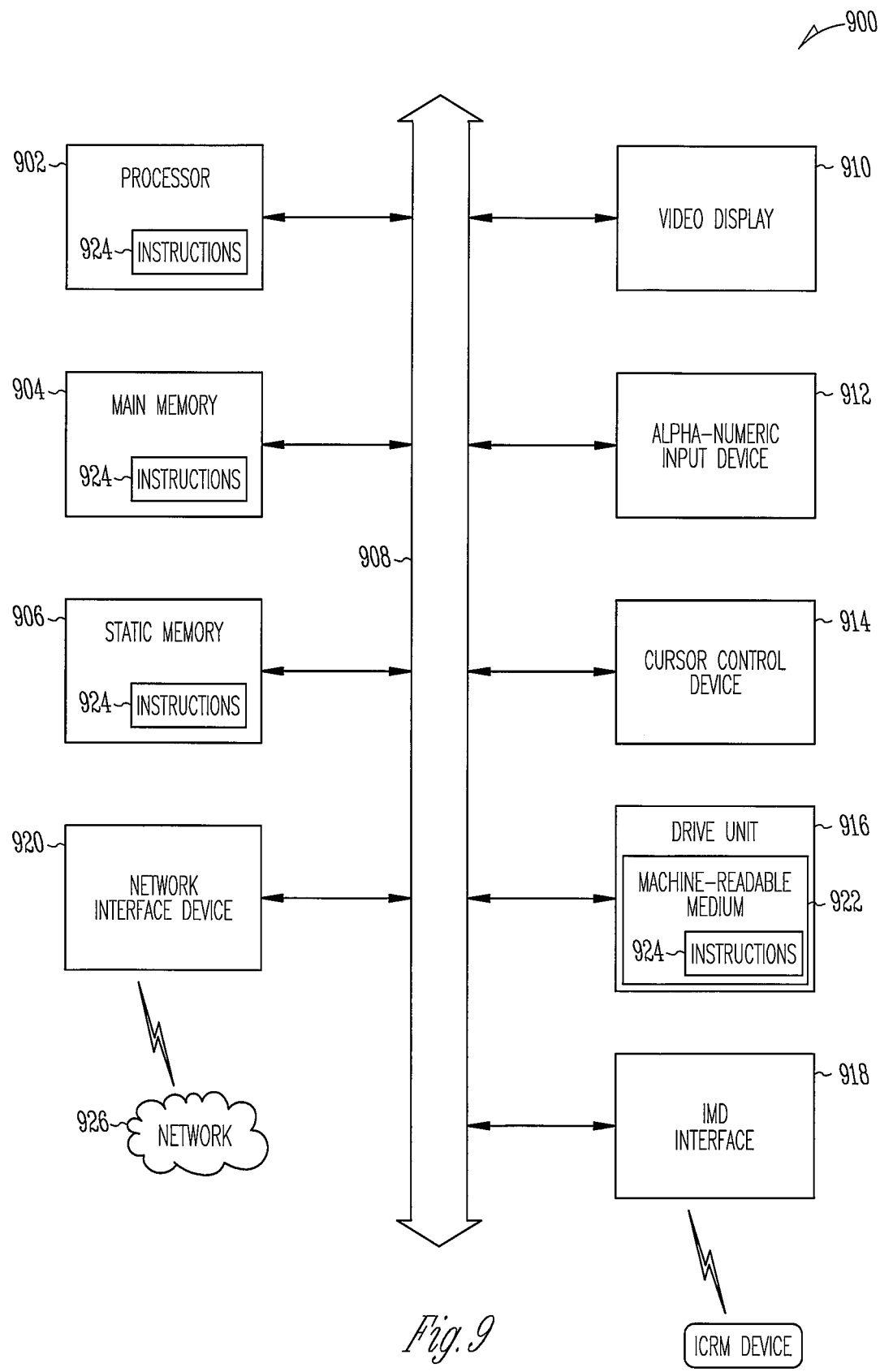
FIG. 9 is a block diagram illustrating an example of an external programming and display device capable of receiving data from an implantable cardiac rhythm management device.

FIG. 9 is a block diagram of machine in the example form of a computer system 900 within which instructions, for causing the machine to perform any one or more of the methodologies discussed herein, can be executed. In certain examples, the machine operates as a standalone device or can be connected (e.g., networked) to other machines. In a networked deployment, the machine can operate in the capacity of a server or a client machine in server-client network environment, or as a peer machine in a peer-to-peer (or distributed) network environment. The machine can be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the machine can include any collection of machines that individually or jointly execute a set (or multiple sets) of instructions to perform any one or more of the methodologies discussed herein.

The example computer system 900 includes a processor 902 (e.g., a central processing unit (CPU), a graphics processing unit (GPU) or both), a main memory 904 and a static memory 906, which communicate with each other via a bus 908. The computer system 900 can further include a video display unit 910 (e.g., a liquid crystal display (LCD) or a cathode ray tube (CRT)). The computer system 900 also includes an alphanumeric input device 912 (e.g., a keyboard), a user interface (UI) navigation device 914 (e.g., a mouse), a disk drive unit 916, an implantable medical device interface 918, and a network interface device 920.

The implantable medical device interface can include a wired or wireless data connection with an implantable medical device. In an example, the implantable medical device (IMD) interface allows information stored in the IMD to be downloaded to the computer system 900 for display or analysis. In an example, the information downloaded from the IMD can be displayed on the video display unit 910. In another example, the information downloaded can be processed by the processor 902 prior to display on the video display unit 910. In an example, the IMD interface can also upload information, including programming parameters for an implantable CRM device, back into the IMD.

Machine-Readable Medium

The disk drive unit 916 includes a machine-readable medium 922 on which can be stored one or more sets of instructions and data structures (e.g., software) 924 embodying or utilized by any one or more of the methodologies or functions described herein. The instructions 924 can also reside, completely or at least partially, within the main memory 904 or within the processor 902 during execution thereof by the computer system 900, the main memory 904 and the processor 1102 also constituting machine-readable media.

While the machine-readable medium 922 can be shown in an example embodiment to be a single medium, the term "machine-readable medium" can include a single medium or multiple media (e.g., a centralized or distributed database, or associated caches and servers) that store the one or more instructions or data structures. The term "machine-readable medium" can include any tangible medium that is capable of storing, encoding or carrying instructions for execution by the machine and that cause the machine to perform any one or more of the methodologies of the present application, or that is capable of storing, encoding or carrying data structures utilized by or associated with such instructions. The term "machine-readable medium" can include, but need not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks including internal hard disks and removable disks; magneto-optical disks; and CD-ROM and DVD-ROM disks.

Transmission Medium

The instructions 924 can further be transmitted or received over a communications network 926 using a transmission medium. The instructions 924 can be transmitted using the network interface device 920 and any one of a number of transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., Wi-Fi and WiMax networks).

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled

What is claimed is:

1. A cardiac rhythm management system, the system comprising:
   an implantable physiological data monitor configured to monitor a plurality of cardiac responses and a physiological parameter including at least one of heart rate, respiration rate, blood pressure, or posture;
   a processor configured to classify the cardiac responses into one of at least three classes including pace-dominant, fusion, and pseudo-fusion classes and calculate statistical information regarding the classified cardiac responses, wherein the pace-dominant, fusion, and pseudo-fusion classes correspond to a cardiac response resulting from a corresponding electrostimulation, wherein the processor is configured to correlate the calculated statistical information with the physiological parameter;
   a memory configured to store the classified cardiac responses, the physiological parameter, and the calculated statistical information for future use by the processor or for display; and
   a display configured to display in a graphical format the calculated statistical information in correlation with the physiological parameter.

2. The cardiac rhythm management system of claim 1, wherein the processor is further configured to use at least one of the cardiac responses stored in the memory to control a parameter of the implantable cardiac rhythm management device.

3. The cardiac rhythm management system of claim 1, wherein the processor is configured to use a series of cardiac responses stored in the memory to control a parameter of the implantable cardiac rhythm management device.

4. The cardiac rhythm management system of claim 1, wherein the processor is further configured to use the statistical information about the cardiac responses stored in the memory to control a parameter of the implantable cardiac rhythm management device.

5. The cardiac rhythm management system of claim 1, wherein the processor is further configured to use the statistical information about the cardiac responses stored in the memory to provide programming recommendations; and
   wherein the display is configured to display the programming recommendations.

6. The cardiac rhythm management system of claim 1, wherein the processor is further configured to use the statistical information about the cardiac responses stored in the memory to send an alert to the display.

7. The cardiac rhythm management system of claim 1, wherein the cardiac responses are measured using electrograms, each electrogram including a depolarization.

8. The cardiac rhythm management system of claim 7, wherein the implantable physiological data monitor is configured to monitor a plurality of sensed intrinsic depolarizations and a plurality of evoked response depolarizations, the processor is configured to classify the plurality of sensed intrinsic depolarizations and the plurality of evoked response depolarizations and calculate statistical information about the plurality of classified depolarizations, and the memory is configured to store at least the statistical information about the plurality of classified depolarizations.

9. The cardiac rhythm management system of claim 8, wherein:
   the memory is configured to store the physiological parameter; and
   an external computing device is configured to correlate the statistics with the physiological parameter and display the results in a graphical format.

10. The cardiac rhythm management system of claim 8, wherein the processor is further configured to classify the depolarizations according to at least one of heart chamber, right versus left side of heart, or atrial versus ventricular heart chamber.

11. The cardiac rhythm management system of claim 8, wherein the processor is further configured to classify the depolarizations by comparing the depolarization morphology to a template stored in the memory, wherein the stored template enables discrimination between classes.

12. A method comprising:
   monitoring, using an implantable cardiac rhythm management device, a plurality of cardiac responses and a physiological parameter including at least one of heart rate, respiration rate, blood pressure, or posture;
   classifying, using a processor, the cardiac responses into one of at least three classes including pace-dominant, fusion, and pseudo-fusion classes, wherein the pace-dominant, fusion, and pseudo-fusion classes correspond to a cardiac response resulting from a corresponding electrostimulation;
   calculating statistical information about the classifications;
   correlating the calculated statistical information with the physiological parameter;
   storing the classified cardiac responses, the physiological parameter, and the calculated statistical information in a memory; and
   displaying in a graphical format on an external device at least the calculated statistical information in correlation with the physiological parameter.

13. The method of claim 12, including programming a parameter of the implantable cardiac rhythm management device using the statistical information about the cardiac responses.

14. The method of claim 12, wherein the calculating includes trending the statistical information over an interval of time.

15. The method of claim 14, wherein the interval of time allows for monitoring, classifying and calculating over a period of time representative of a chronic condition.

16. The method of claim 12, wherein the displaying includes numeric displays and graphical displays.

17. The method of claim 12, wherein monitoring a plurality of cardiac responses includes collecting electrograms associated with each cardiac response, wherein each electrogram includes a depolarization.

18. The method of claim 17, wherein the monitoring comprises monitoring a plurality of sensed intrinsic depolarizations and a plurality of evoked response depolarizations, the classifying comprises classifying the plurality of sensed intrinsic depolarizations and the plurality of evoked response depolarizations, and calculating statistical information about the classifications.

19. The method of claim 17, wherein the classifying the depolarizations comprises also classifying according to at least one of heart chamber, right versus left side of heart, or atrial versus ventricular heart chamber.

20. The method of claim 17, wherein the classifying the depolarizations comprises comparing each depolarization morphology to a stored template, wherein the stored template enables discrimination between the classes.

21. The method of claim 17, wherein the classifying the depolarization comprises comparing a depolarization morphology to a plurality of stored templates, wherein each stored template enables identification of one or more of the classes.

22. The method of claim 12, further including automatically programming a parameter of the implantable cardiac rhythm management device using the calculated statistical information; and wherein the programmed parameter is displayed in association with the calculated statistical information used to program the parameter.

* * * * *